United States Patent
Danylyk

(10) Patent No.: US 6,443,975 B1
(45) Date of Patent: Sep. 3, 2002

(54) BIOENERGY INSTRUMENT

(76) Inventor: Donald Danylyk, 1538 Ohio Ave., Virginia Beach, VA (US) 23454

( * ) Notice: Subject to any disclaimer, the term of this patent is extended or adjusted under 35 U.S.C. 154(b) by 0 days.

(21) Appl. No.: 09/386,479

(22) Filed: Aug. 31, 1999

(51) Int. Cl.[7] .................................................. A61N 5/06
(52) U.S. Cl. ........................................... 607/88; 607/94
(58) Field of Search ............................. 607/88, 90, 91, 607/92, 93

(56) References Cited

U.S. PATENT DOCUMENTS

| | | |
|---|---|---|
| 5,092,835 A | 3/1992 | Schurig et al. |
| 5,183,456 A | 2/1993 | Liboff et al. |
| 5,458,142 A | 10/1995 | Farmer et al. |
| 5,643,333 A * | 7/1997 | Yun .............................. 607/88 |
| 5,786,893 A | 7/1998 | Fink et al. |
| 5,862,165 A | 1/1999 | Handa et al. |

FOREIGN PATENT DOCUMENTS

| | | | |
|---|---|---|---|
| EP | 01-893-29 | * 7/1986 | ........... A61B/17/22 |
| JP | 5-190958 | 7/1993 | |

* cited by examiner

*Primary Examiner*—Michael Peffley
(74) *Attorney, Agent, or Firm*—Michael L. Greenberg Esq.; Greenberg & Lieberman

(57) ABSTRACT

The present invention relates generally to the bioenergy field. Acupuncture is an example of this bioenergy; in acupuncture, this bioenergy is known as Chi. There are many other names for this bioenergy, such as prana, etheric field, aura, aka, etc. This invention relates to a new and novel way of influencing these bioenergies.

11 Claims, 1 Drawing Sheet

BIOENERGY INSTRUMENT

Reference is hereby made to Document Disclosure No. 438606 filed on Jul. 8, 1998.

FIELD OF THE INVENTION

The present invention relates generally to the bioenergy field of which acupuncture is an example. The bioenergy known to acupuncture is called Chi, but many other names for bioenergy have been used in the past such as prana, etheric field, aura, aka, etc. This invention relates to a new and novel way of influencing these bioenergies.

BACKGROUND OF THE PRESENT INVENTION

Acupuncture has been employed to heal and promote balance and harmony for thousands of years. Today, this ancient Chinese practice is gaining more and more respect in the medical community. Traditionally, acupuncture is used specifically to treat injuries and ailments, but today, many people use acupuncture to promote overall balance and harmony in their lives.

In U.S. Pat. No. 5,458,142, issued to Farmer, et al. on Oct. 17, 1995, a brief description of the acupuncture and the bioenergy field is offered. Acupuncture works on the premise that certain points in the body control and release energy. Needles are used at various points to influence a person's bioenergy. Acupuncture techniques have developed over years, but essentially, the methods practiced have remained constant. However, with acupuncture being used to treat specific ailments and injuries and promote overall balance and harmony in people's lives, there is a definite need for modern-day bioenergy techniques that are less painful and more effective.

SUMMARY OF THE INVENTION

Therefore a need has been established for a bioenergy instrument that relates to an instrument for the medical field that improves the health of living beings by means of impinging a principal line of the atomic spectrum of an element upon that element to produce an exit energy that affects living beings. This exit energy is not light, but a type of new energy with some characteristics different from light.

One object of the present invention is to influence the bioenergy field to produce a state of balance and harmony within the patient. The present invention does not have to be used at an acupuncture point to balance the bioenergy. The invention could be placed on the body and it would balance the bioenergy of the entire body. This illustration in the acupuncture field is only one of many fields that would benefit from the invention. Because other forms of treatment are used to treat chemical, perceived, or direct imbalance in a person, the present invention could be used to compliment or replace existing treatments of psycho-therapy, pain management, stress management, relaxation therapy, meditation, and alternative therapy.

The invention operates on the discovery that if a wavelength of light, corresponding to a principal line in the atomic spectrum of an element, is impinged on this element then there is produced an exit energy that affects a living being as well as the bioenergy. For example, it is known in physics that an important principle line in the atomic spectrum of the element aluminum is 396.15 nanometers (nm). If light at this wavelength of 396.15 nm is impinged upon aluminum, there is produced a force that will affect the bioenergy. As another example, for silver, a principal line in the atomic spectrum is known to be 328.07 nm. If this wavelength of light is impinged upon silver, there will be produced an exit energy that will affect an organism as well as the bioenergy. This discovery appears to also apply to all other elements. The list of these elements appears in what is called the periodic chart in the field of chemistry.

The invention is, of course, not limited to specific embodiments described and illustrated but may be realized in various modifications, substitutions, adaptations or combinations without departing for the spirit and scope of the appended claims.

DETAILED DESCRIPTION OF THE PREFERRED EMBODIMENTS

Figure 1:
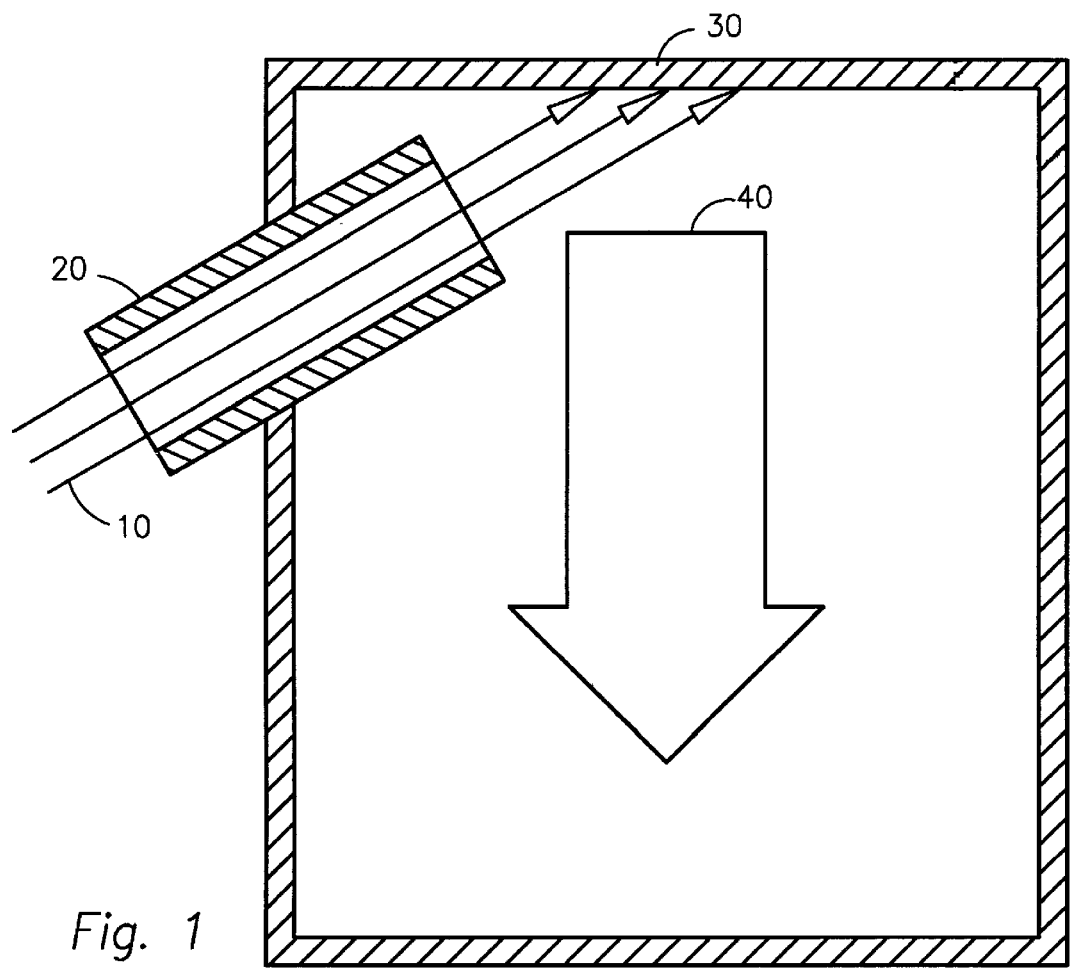
FIG. 1 shows a first embodiment of the present invention.

FIG. 1 shows one of many methods by which the invention could be made. In FIG. 1, the element used will be silver for illustration purposes. A source of light at 328.07 nm (1) passes through a tube (2) and impinges on the walls of a silver container (3). The exit energy (4) is produced by the particular wavelength of light impinging on the element. The exit energy (4), which is yet to be defined in science, could affect a living being.

Figure 2:
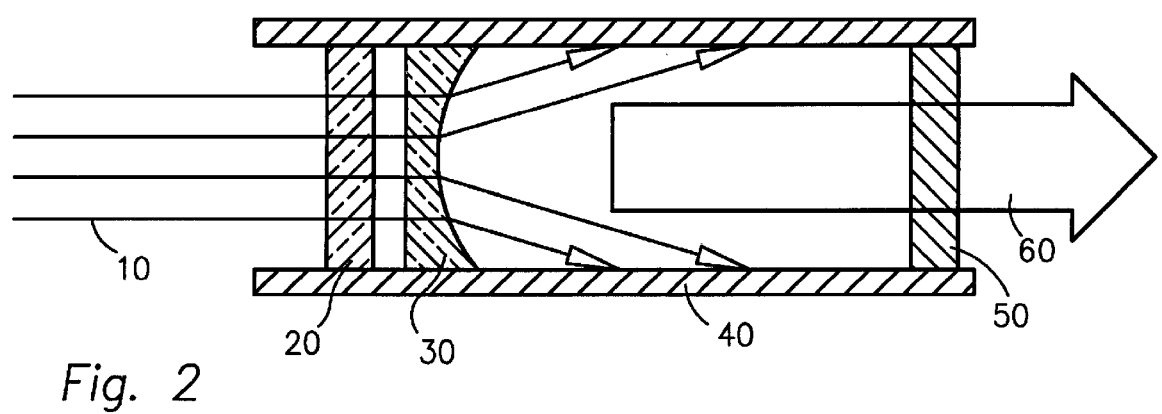
FIG. 2 shows a second embodiment of the present invention.

FIG. 2 shows another method by which the invention could be made. In FIG. 2, the element used will be aluminum for illustration purposes. A source of light rays (10), as from a light bulb, is passed through a narrowband optical interference filter (20) which is designed to pass light at the 396.15 nm principal line of aluminum. By experimentation, it was found that for best filter design, keeping the full width of the pass band, measured at one-half the peak transmittance, at less than 3 nm was important—that is, more exit energy (60) was produced according to this scheme. The 396.15 nm light then passes through the concave optical lens (30) which directs the light to impinge on the walls of the aluminum tube (40). A cork plug (50) is used to keep other light from entering the tube, while also permitting the exit energy (60) to pass through to the outside of the invention to affect a living being. However, any plug could be employed so long as it is opaque and allows the exit energy (60) to pass. It was discovered that if outside light is allowed to leak into the present invention, outside light will diminish or eliminate production of the exit energy (60). The present invention is more effective when the living being is closer to the cork plug (50).

To those persons skilled in optics and physics, it is apparent that the present invention could be realized in many different forms and sizes. For example, light from a monochromator or laser could be used instead of an interference filter (20). Also, any other element such as silver, gold, platinum, copper, etc. could be used with the proper optical interference filter (20). In addition, for expensive elements, the container (3) or (40) does not have to be made of the element as only a thin surface is needed for the light to impinge on. The concave lens (30) is simply used to direct light toward the element, and any device that does the same could be substituted such as mirrors or a light diffuser.

The concave lens (30) can also impinge light on a conventional chemical compound which contains the element.

The weak lines of the atomic spectrum typically do not produce a strong exit energy, therefore the principal lines are the preferred choice. Sometimes, the principal lines of the atomic spectrum are in the ultraviolet region, making the instrument technologically difficult or very expensive to manufacture. Then, the strongest line in a useable range of the atomic spectrum can be substituted. As an illustration, the 460.75 nm line of the element gold could be used because the principle lines of the atomic spectrum are in the ultraviolet region.

The exit energy from this invention was found to be able to pass through non-metallic substances such as cork, wood, clothes, heavy winter coats and some metals, and still be able to affect the human body. When a human body is affected by the exit energy, people experience various sensations which they describe as pulsations, waves, tightness, heat, coolness, tingling feelings, rush of energy, wonderful relaxed sense of well-being, blissful joy, peace, and contentment. With repeated long term use of once or twice a day, people reported improvements or healing of the following health problems: sore throat, sinus problems, incurable skin rash problems, eyesight problems, lung problems, kidney problems, diabetes, cancer, pain in knees and joints, inflexible stiff fingers, irregular heart beat, hearing problems, pain along spine, pain after surgery, headaches, stressful feelings, sleeplessness, depression, psychological problems, nervous tensions, uncontrolled twitching of hands, tension in back of neck, travel sickness, and many other conditions. It appears the exit energy from the invention can improve almost any health problem without any side effects. As human beings are concerned, the invention can treat many kinds of diseases and maintain good health to a certain extent. The same functions can also be applied to other species of living beings.

Up to the present, efforts have been made to control, affect or treat diseases and psychosomatic disorders by only physical methods. The invention provides another method to improve health and well-being which can complement other methods.

The invention is, of course, not limited to specific embodiments described and illustrated but may be realized in various modifications, substitutions, adaptations or combinations without departing for the spirit and scope of the appended claims.

I claim:

1. An apparatus for affecting living beings, comprising:
   a means for producing a light at a principal line of the atomic spectrum of an element;
   a means for impinging the light onto the element to produce an exit energy;
   a means for greater production of said exit energy by keeping the full width of the passband, measured at one half the peak transmittance
   around the principal line to less than 3 nm;
   and a means for permitting the exit energy to reach a living being.

2. The apparatus of claim 1, wherein said means for producing light does so at a line of strong intensity of the atomic spectrum of an element.

3. A bioenergy producing apparatus, comprising:
   a light source;
   a container, receiving light from said light source;
   an element, impinged by a principal line of the atomic spectrum of said element from said light source, to produce an exit energy; and
   a means for greater production of said exit energy by keeping the full width of the passband, measured at one half the peak transmittance, around the principal line of said element to less than 3 nm.

4. The apparatus of claim 3, further comprising a concave optical lens which directs light from said light source to impinge said element with the principle line of the wavelength.

5. The apparatus of claim 3, wherein said element is enclosed within said container.

6. The apparatus of claim 3, wherein said container incorporates said element.

7. The apparatus of claim 3, wherein said container is plugged with an opaque member, wherein said opaque member is said means for preventing other wavelengths from impinging on the element.

8. The apparatus of claim 7, wherein said opaque member is a cork.

9. A bioenergy producing apparatus, comprising:
   a light source;
   a narrow band optical interference filter, filtering light from said light source;
   an element, impinged by the light from said light source after the light from said light source has been filtered by said narrow band optical interference filter;
   a means for greater production of exit energy by keeping the full width of the passband, measured at one half the peak transmittance, around the principal line of said element to less than 3 nm.

10. A bioenergy producing apparatus, comprising:
    a light source;
    a narrow band optical interference filter, filtering light from said light source;
    an element, impinged by the light from said light source after the light from said light source has been filtered by said narrow band optical interference filter;
    wherein said filter is designed for greater production of exit energy by keeping the full width of the pass band, measured at one-half the peak transmittance, at less than 3 nm.

11. The apparatus of claim 3, wherein said container is plugged with an opaque member, wherein said opaque member permits exit energy to pass from said container.

* * * * *